United States Patent [19]

Esanu

[11] Patent Number: 4,659,719
[45] Date of Patent: Apr. 21, 1987

[54] 6-PHENETHYLAMINOALKYL-FURO-(3,4-C)-PYRIDINE DERIVATIVES AND THERAPEUTIC COMPOSITIONS CONTAINING THE SAME

[75] Inventor: André Esanu, Paris, France

[73] Assignee: Societe de Conseils de Recherches et d'Applications Scientifiques (S.C.R.A.S.), Paris, France

[21] Appl. No.: 789,731

[22] Filed: Oct. 21, 1985

[30] Foreign Application Priority Data

Oct. 27, 1984 [GB] United Kingdom ............... 8427218

[51] Int. Cl.$^4$ .................. A61K 31/44; C07D 491/048
[52] U.S. Cl. ..................................... 514/302; 546/116
[58] Field of Search .................... 546/116; 514/302

[56] References Cited

PUBLICATIONS

Bockmühl et al., Annalen, vol. 561, pp. 52–58 & 69–73, (1949).

Primary Examiner—Henry R. Jiles
Assistant Examiner—Bernard I. Dentz
Attorney, Agent, or Firm—Lucas & Just

[57] ABSTRACT

This invention relates to new 1,3-dihydro-6-[1-cyano-1-isopropyl-N-phenethyl-N-methyl-ω-aminoalkyl]-7-hydroxy-furo-(3,4-c)-pyridine derivatives of the general formula

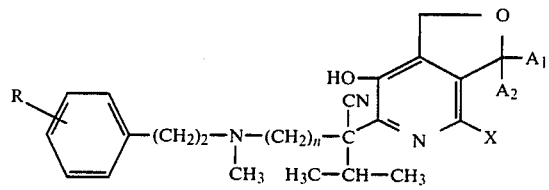

wherein each of $A_1$ and $A_2$ independently represents various substituents and to pharmaceutically acceptable salts of said derivatives, to a process for the preparation of the same, comprising reacting, in stoichiometric proportions, at 15°–65° C., in dimethylsulphoxide, a 6-(1-cyano-2-methyl-propyl)-7-hydroxy-furo-(3,4-c)-pyridine derivative with the appropriate N-methyl-N-phenethyl-ω-aminoalkyl choride and, finally, to a therapeutic composition of matter comprising as an essential ingredient therein any of said compounds in an amount effective to act as a calcium antagonist or a serotonin antagonist together with an appropriate diluent or carrier.

3 Claims, No Drawings

6-PHENETHYLAMINOALKYL-FURO-(3,4-C)-PYRIDINE DERIVATIVES AND THERAPEUTIC COMPOSITIONS CONTAINING THE SAME

The invention relates to new 6-phenethylaminoalkyl-7-hydroxy-furo-(3,4-c)-pyridine derivatives, to a process for their preparation and to therapeutic compositions containing them.

The invention provides 1,3-dihydro-6-[1-cyano-1-isopropyl-N-phenethyl-N-methyl-ω-aminoalkyl]-7-hydroxy-furo-(3,4-c)-pyridine derivatives of the general formula I:

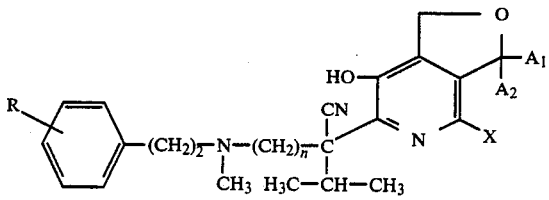

wherein, each of $A_1$ and $A_2$ independently represents a hydrogen atom, a straight chain saturated or unsaturated hydrocarbon group having from 1 to 5 carbon atoms, a heterocyclic group having up to 6 ring atoms, a carbomonocyclic group, a phenylalkyl group or a phenylalkenyl group, each of the groups represented by $A_1$ to $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α or β-alkoxy-N-pyrrolidinyl groups in which the alkoxy group has from 1 to 5 carbon atoms; R represents from one to three methoxy groups; n is 2,3,4 or 5; and X represents a hydrogen or chlorine atom; and further provides pharmaceutically acceptable salts of such compounds.

The compounds according to the invention are of interest for their therapeutical activity, principally in the field of calcium antagonism and serotoninergic receptors.

The invention also provides a process for the preparation of the compounds according to the invention, this process comprising reacting in stoichiometric proportions, at 15°–65° C. in dimethylsulphoxide, a 6-(1-cyano-2-methyl-propyl)-7-hydroxy-furo-(3,4-c)-pyridine derivative of the general formula II

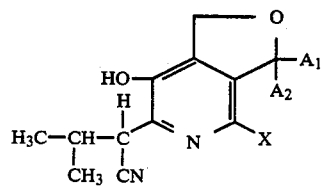

wherein $A_1$, $A_2$ and X have the above meanings with an N-methyl-N-phenethyl-ω-aminoalkyl chloride of the general formula III

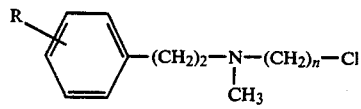

wherein R and n have the above meanings.

The 6-(1-cyano-2-methyl-propyl)-7-hydroxy-furo-(3,4-c)-pyridine derivatives II may be obtained from corresponding 6-methyl-7-hydroxy derivatives of the general formula IV, disclosed in our previous U.S. Pat. No. 4,383,998 and patents application Ser. Nos. 593,700 and 661,376.

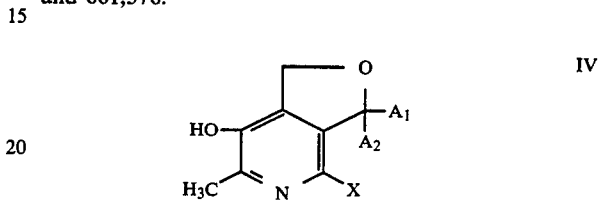

wherein $A_1$, $A_2$ and X have the above meanings by the following sequence of reactions:

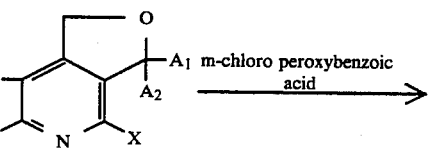

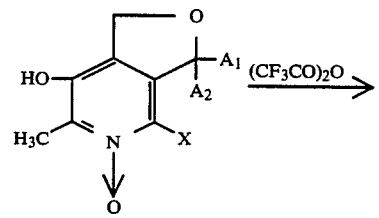

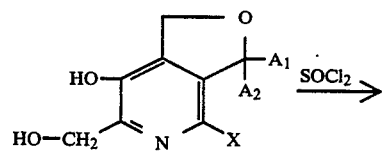

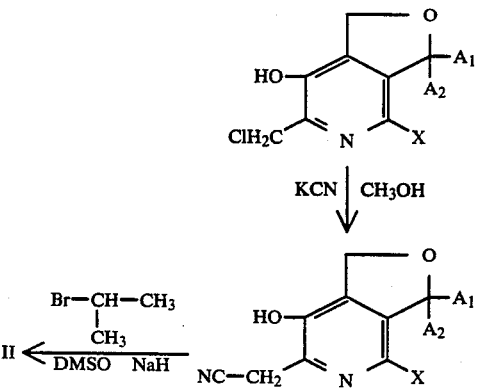

The preparation of one only of the starting compounds II, 1,3-dihydro-3-methyl-6-(1-cyano-2-methyl-propyl)-7-hydroxy-furo-(3,4-c)-pyridine, is now described in detail, other starting materials being obtained by the same way.

(a) In a one liter reactor fitted with stirring, warming and cooling means, 18.2 g (0.11 mol) of 1,3-dihydro-3,6-dimethyl-7-hydroxy-furo-(3,4-c)-pyridine were treated at 0° C., in the presence of 300 ml of methylene dichloride, with 22.5 g of m-chloroperoxybenzoic acid, slowly added. After stirring overnight at room temperature, there were added 150 ml of 10% sodium sulphate solution. After stirring and decantation, the product was washed with the same amount of sodium sulphate solution, twice with 150 ml of sodium bicarbonate solution and three times with 100 ml of water, and then dried over anhydrous sodium sulphate. On evaporation to dryness, there was obtained a beige precipitate which was washed with petroleum ether, hexane, then filtered and dried. Yield 18.9 g (95%) of 1,3-dihydro-3,6-dimethyl-7-hydroxy-furo-(3,4-c)-pyridine-N-oxide.

(b) In the same reactor as above, the 18.9 g of compound obtained in the previous step were treated at 0°–5° C., in the presence of 175 ml of methylene dichloride, with 5 ml of trifluoroacetic anhydride added dropwise under stirring. The mixture was stirred overnight at room temperature, and then cooled and treated dropwise with 110 ml of methanol. After evaporation to dryness, the residue was taken up in 350 ml of chloroform, washed twice with 100 ml of 10% sodium bicarbonate solution and three times with 150 ml of water and dried on anhydrous sodium sulphate. The chloroform was evaporated off and the residue was washed with diethyl ether and dried under reduced pressure. Yield 18 g (95%) of 1,3-dihydro-3-methyl-6-hydroxymethyl-7-hydroxy-furo-(3,4-c)-pyridine.

(c) In a two liter reaction fitted as above and under nitrogen circulation, the 18 g of the previously obtained compound were stirred with 350 ml of dry benzene; there were slowly added 6 ml of thionyl chloride under stirring at room temperature. The resultant mixture was warmed at 70° C. for one hour, leading to a yellow precipitate. This was separated off, washed with benzene and then with diethyl ether, and dissolved in 400 ml of methylene dichloride. The solution was washed with 10% sodium bicarbonate solution until pH 8, washed with water, treated with carbon black, filtered, and concentrated up to crystallization. The product was separated off, washed twice with diethyl ether and dried, giving 19.2 g (yield 96%) of 1,3-dihydro-3-methyl-6-chloromethyl-7-hydroxy-furo-(3,4-c)-pyridine.

(d) The 19.2 g of the compound obtained in the previous step were treated in a two liter reactor by 6.6 g of potassium cyanide in the presence of 0.8 liter of methanol at 28°–30° C., under reflux for 18 hours. After separation, filtration, washing with chloroform, the solution was evaporated to dryness and the residue treated with pentane. There was thus obtained 17.5 g (95%) of 1,3-dihydro-3-methyl-6-cyanomethyl-7-hydroxy-furo-(3,4-c)-pyridine.

(e) Into the same reactor as above, and under nitrogen circulation, 4.27 g (0.09 mol) of 50% sodium hydride in oil were poured, then washed in situ with hexane. There were poured 50 ml of dry dimethylsulphoxide and then, dropwise under stirring, the 17.5 g of the compound of previous step; the mixture was stirred for one hour at room temperature and there was slowly added, under stirring 9.5 ml (0.12 mol) of isopropyl bromide. The reaction mixture was stirred for two hours at room temperature, then slowly poured onto icy water. After extraction with methylene dichloride and washing with water, there was obtained after filtration and concentration, a residue which was recrystallized from diethyl ether and dried. Yield 16.2 g (74%) of compound II wherein $A_1$ stands for methyl and $A_2$ stands for hydrogen.

The invention further provides a therapeutical composition comprising a 1,3-dihydro-6-(1-cyano-1-isopropyl-N-phenethyl-N-methyl-ω-aminoalkyl)-7-hydroxy-furo-(3,4-c)-pyridine derivative of the general formula I as above defined or a pharmaceutically acceptable salt thereof in admixture with a therapeutically acceptable diluent or carrier.

The following examples illustrate the invention.

EXAMPLE 1

1,3-dihydro-3-methyl-6-[1-cyano-1-isopropyl-3-N-(m,p-dimethoxy-phenethyl)-N-methyl-3-aminopropyl]-7-hydroxy-furo-(3,4-c)-pyridine $R = (OCH_3)_2$
$n = 2$
$X = H$
$A_1 = CH_3$
$A_2 = H$ Into the same reactor as in step (e) above, and under nitrogen circulation, 4.8 g (0.1 mol) of 50% sodium hydride in oil were poured and then washed in situ with hexane. 150 ml of dry dimethylsulphoxide was then poured into the reactor followed, slowly under stirring, by 21.8 g (0.1 mol) of 1,3-dihydro-3-methyl-6-(1-cyano-2-methyl-propyl)-7-hydroxy-furo-(3,4-c)-pyridine. The mixture was stirred for one hour at room temperature and there was slowly added, under stirring, 26 g (0.10 mol) of N-(3,4-dimethoxy-phenethyl)-N-methyl-2-aminoethyl chloride dissolved in 100 ml of dry dimethylsulphoxide. The reaction mixture was stirred for two hours at room temperature, and then slowly poured on icy water. After extraction with methylene dichloride, washing with water and treatment with hydrochloric acid, there was obtained after filtration and concentration a residue, which was recrystallized from diethyl ether and dried. Yield 23 g (47%) of a white crystalline powder melting at 167° C. (Tottoli), elemental analysis of which showed a very good correspondence with the formula $C_{26}H_{35}N_3O_4$, HCl.

EXAMPLE 2

1,3-dihydro-3-phenyl-4-chloro-6-[1-cyano-1-isopropyl-N-(m,p-dimethoxy-phenethyl)-N-methyl-3-aminopropyl]-7-hydroxy-furo-(3,4-c)-pyridine $R = (OCH_3)_2$
$n = 2$
$X = Cl$
$A_1 = C_6H_5$
$A_2 = H$ The method of example 1 was repeated with 1,3-dihydro-3-phenyl-4-chloro-6-(1-cyano-2-methyl-propyl)-7-hydroxy-furo-(3,4-c)-pyridine and the same 2-aminoethyl chloride at 35°–40° C. Yield was 31.5 g (54%) of a white powder melting at 187°–190° C. (Tottoli), elemental analysis of which showed a good correspondence with the formula $C_{31}H_{36}N_3O_4Cl$, HCl.

EXAMPLE 3

1,3-dihydro-3-methyl-3-α-furyl-6-[1-cyano-1-isopropyl-N-(m,p-dimethoxy-phenethyl)-N-methyl-3-amino-propyl]-7-hydroxy-furo-(3,4-c)-pyridine $R=(OCH_3)_2$
$n=2$
$X=H$
$A_1=CH_3$
$A_2=\alpha$-furyl The method of example 1 was repeated with 1,3-dihydro-3-methyl-3-α-furyl-6-(1-cyano-2-methyl-propyl)-7-hydroxy-furo-(3,4-c)-pyridine and the same 2-aminoethyl chloride at room temperature. Yield was 22 g (39.5%) of a white product melting at 173°–175° C. (Tottoli), elemental analysis of which showed a very good correspondence with the formula $C_{30}H_{37}N_3O_5$, HCl.

EXAMPLE 4

1,3-dihydro-3-propyl-4-chloro-6-[1-cyano-1-isopropyl-N-(m,p-dimethoxy-phenethyl)-N-methyl-4-aminobutyl]-7-hydroxy-furo-(3,4-c)-pyridine $R=(OCH_3)_2$
$n=3$
$X=Cl$
$A_1=$propyl
$A_2=H$ The method of example 1 was repeated but with 1,3-dihydro-3-propyl-4-chloro-6-(1-cyano-2-methyl-propyl)-7-hydroxy-furo-(3,4-c)-pyridine and N-(3,4-dimethoxy-phenethyl)-N-methyl-3-aminopropyl chloride at 50° C. but without final acidic treatment. Yield was 30.7 g (58%) of a white product melting at 144° C. (Tottoli), elemental analysis of which showed a perfect correspondence with the formula $C_{29}H_{40}N_3O_4Cl$.

EXAMPLE 5

1,3-dihydro-3-phenyl-6-[1-cyano-1-isopropyl-N-(m,p-dimethoxy-phenethyl)-N-methyl-4-aminobutyl]-7-hydroxy-furo-(3,4-c)-pyridine $R=(OCH_3)_2$
$N=3$
$X=H$
$A_1=$phenyl
$A_2=H$ The method of example 4 was repeated but with 1,3-dihydro-3-phenyl-6-(1-cyano-2-methyl-propyl)-7-hydroxy-furo-(3,4-c)-pyridine and the same 3-aminopropyl chloride at 65° C.; final acidic treatment was with oxalic acid. Yield 26 g (42%) of a yellow powder melting at 186°–190° C. (Tottoli), elemental analysis of which showed a very good correspondence with the formula $C_{32}H_{39}N_3O_4$, $C_2H_2O_4$.

EXAMPLE 6

1,3-dihydro-3-p-fluorophenyl-6-[1-cyano-1-isopropyl-N-(m,p-dimethoxy-phenethyl)-N-methyl-4-aminobutyl]-7-hydroxy-furo-(3,4-c)-pyridine $R=(OCH_3)_2$
$n=3$
$X=H$
$A_1=$p-fluorophenyl
$A_2=H$ The method of example 5 was repeated, the only change being that the first starting material was 1,3-dihydro-3-p-fluorophenyl-6-(1-cyano-2-methyl-propyl)-7-hydroxy-furo-(3,4-c)-pyridine. Yield was 40 1 g (63%) of a white powder melting at 182' C. (Tottoli), elemental analysis of which showed a very good correspondence with the formula $C_{32}H_{38}N_3O_4F$, $C_2H_2O_4$.

EXAMPLE 7

1,3-dihydro-3-p-trifluoromethylphenyl-4-chloro-6-[1-cyano-1-isopropyl-N-(m,m,p-trimethoxy-phenethyl)-N-methyl-4-aminobutyl]-7-hydroxy-furo-(3,4-c)-pyridine $R=(OCH_3)_3$
$N=3$
$X=Cl$
$A_1=$p-$CF_3$-phenyl
$A_2=H$ The method of example 1 was repeated but starting with 1,3-dihydro-3-p-trifluoromethylphenyl-4-chloro-6-(1-cyano-2-methyl-propyl)-7-hydroxy-furo-(3,4-c)-pyridine and N-(3,4,5-trimethoxy-phenethyl)-N-methyl-3-aminopropyl chloride at 35° C. Yield was 34.7 g (51%) of a yellowish product melting at 204°–207° C. (Tottoli), elemental analysis of which showed a very good correspondence with the formula $C_{34}H_{39}N_3O_4ClF_3$, HCl.

EXAMPLE 8

1,3-dihydro-3-p-methoxyphenyl-6-[1-cyano-1-isopropyl-N-(m,p-dimethoxy-phenethyl)-N-methyl-4-aminobutyl]-7-hydroxy-furo-(3,4-c)-pyridine $R=(OCH_3)_2$
$n=3$
$X=H$
$A_1=$p-methoxyphenyl
$A_2=H$ The method of example 4 was repeated but starting with 1,3-dihydro-3-p-methoxy-phenyl-6-(1-cyano-2-methyl-propyl)-7-hydroxy-furo-(3,4-c)-pyridine and the same 3-aminopropyl chloride at 60° C. Yield was 20 g (36%) of a white powder melting at 214°–217° C. (Tottoli), elemental analysis of which showed a good correspondence with the formula $C_{33}H_{41}N_3O_5$.

EXAMPLE 9

1,3-dihydro-3-(p-[α-methoxy-N-pyrrolidinyl]-phenyl)-6-[1-cyano-1-isopropyl-N-(m,p-dimethoxy-phenethyl)-N-methyl-4-amino buty]-7-hydroxy-furo-(3,4-c)-pyridine $R=(OCH_3)_2$
$n=3$
$X=H$
$A_1=$p-(α-methoxy-N-pyrrolidinyl)-phenyl
$A_2=H$ The method of example 5 was repeated but starting with 1,3-dihydro-3-(p-[α-methoxy-N-pyrrolidinyl]-phenyl)-6-(1-cyano-2-methyl-propyl)-7-hydroxy-furo-(3,4-c)-pyridine and the same 3-aminopropyl chloride at 45° C. Yield was 33 g (46%) of a pale beige powder melting at 169°–171° C. (Tottoli), elemental analysis of which showed a very good correspondence with the formula $C_{37}H_{48}N_4O_5$, $C_2H_2O_4$.

EXAMPLE 10

1,3-dihydro-3-methyl-3-butyl-6-[1-cyano-1-isopropyl-N-(m,p-dimethoxy-phenethyl)-N-methyl-4-aminobutyl]-7-hydroxy-furo-(3,4-c)-pyridine $R=(OCH_3)_2$
$n=3$
$X=H$
$A_1=CH_3$
$A_2=$butyl The method of example 5 was repeated but with 1,3-dihydro-3-methyl-3-butyl-6-(1-cyano-2-methyl-propyl)-7-hydroxy-furo-(3,4-c)-pyridine and the same 3-aminopropyl chloride at 30° C. Yield was 27 g (44%) of a white powder melting at 158° C. (Tottoli), elemental analysis of which showed a very good correspondence with the formula $C_{31}H_{45}N_3O_4, C_2H_2O_4$.

EXAMPLE 11

1,3-dihydro-3-methyl-3-phenyl-6-[1-cyano-1-isopropyl-N-(m,m,p-trimethoxy-phenethyl)-N-methyl-4-aminobutyl]-7-hydroxy-furo-(3,4-c)-pyridine $R=(OCH_3)_3$
$n=3$
$X=H$
$A_1=CH_3$
$A_2=$phenyl The method of example 7 was repeated but with 1,3-dihydro-3-methyl-3-phenyl-6-(1-cyano-2-methyl-propyl)-7-hydroxy-furo-(3,4-c)-pyridine and the same 3-aminopropyl chloride at room temperature. Yield was 40 g (66%) of a yellowish product melting at 188°–189° C. (Tottoli), elemental analysis of which showed a very good correspondence with the formula $C_{36}H_{43}N_3O_5$, HCl.

EXAMPLE 12

1,3-dihydro-3-methyl-3-α-thienyl-6-[1-cyano-1-isopropyl-N-(m,p-dimethoxy-phenethyl)-N-methyl-4-aminobutyl]-7-hydroxy-furo-(3,4-c)-pyridine $R=(OCH_3)_2$
$n=3$
$X=H$
$A_1=CH_3$
$A_2=$α-thienyl The method of example 8 was repeated but starting with 1,3-dihydro-3-methyl-3-α-thienyl-6-(1-cyano-2-methyl-propyl)-7-hydroxy-furo-(3,4-c)-pyridine and the same 3-aminopropyl chloride at 55° C. Yield was 29.1 g (53%) of a white powder melting at 147°–149° C. (Tottoli), elemental analysis of which showed a good correspondence with the formula $C_{31}H_{39}N_3O_4S$.

EXAMPLE 13

1,3-dihydro-3-vinyl-3-(p-methylthio-phenyl)-4-chloro-6-[1-cyano-1-isopropyl-N-(m,m,p-trimethoxy-phenethyl)-N-methyl-4-aminobutyl]-7-hydroxy-furo-(3,4-c)-pyridine $R=(OCH_3)_3$
$n=3$
$X=Cl$
$A_1=$vinyl
$A_2=$p-methylthio-phenyl The method of example 7 was repeated but starting with 1,3-dihydro-3-vinyl-3-(p-methylthio-phenyl)-4-chloro-6-(1-cyano-2-methyl-propyl)-7-hydroxy-furo-(3,4-c)-pyridine and the same 3-aminopropyl chloride at 60° C. Yield was 40.7 g (58%) of a pale yellow product melting at 176°–178° C. (Tottoli), elemental analysis of which showed a very good correspondence with the formula $C_{36}H_{44}N_3O_5SCl$, HCl.

EXAMPLE 14

1,3-dihydro-3-phenyl-3-(p-diethylaminoethoxy-phenyl)-6-[1-cyano-1-isopropyl-N-(m,p-dimethoxy-phenethyl)-N-methyl-4-aminobutyl]-7-hydroxy-furo-(3,4-c)-pyridine $R=(OCH_3)_2$
$n=3$
$X=H$
$A_1=$phenyl
$A_2=$p-diethylaminoethoxy-phenyl The method of example 5 was repeated but with 1,3-dihydro-3-phenyl-3-(p-diethylaminoethoxy-phenyl)-6-(1-cyano-2-methyl-propyl)-7-hydroxy-furo-(3,4-c)-pyridine and the same 3-aminopropyl chloride, at 40° C. but acidic treatment was with hydrochloric acid. Yield was 30.5 g (41%) of a white powder melting at 143°–146° C. (Tottoli), elemental analysis of which showed a good correspondence with the formula $C_{43}H_{54}N_4O_5$, HCl.

EXAMPLE 15

1,3-dihydro-3-ethyl-4-chloro-6-[1-cyano-1-isopropyl-N-(m,p-dimethoxy-phenetyl)-N-methyl-5-aminopentyl]-7-hydroxy-furo-(3,4-c)-pyridine $R=(OCH_3)_2$
$n=4$
$X=H$
$A_1=$ethyl
$A_2=H$ The method of example 1 was repeated but with 1,3-dihydro-3-ethyl-4-chloro-6-(1-cyano-2-methyl-propyl)-7-hydroxy-furo-(3,4-c)-pyridine and N-(3,4-dimethoxyphenethyl)-N-methyl-4-aminobutyl chloride at 55° C. Yield was 26 g (46%) of a pale yellow powder melting at 218° C. (Tottoli), elemental analysis of which showed a good correspondence with the formula $C_{29}H_{40}N_3O_4Cl$, HCl.

EXAMPLE 16

1,3-dihydro-3,3-diphenyl-4-chloro-6-[1-cyano-1-isopropyl-N,(m,m,p-trimethoxy-phenethyl)-N-methyl-5-aminopentyl]-7-hydroxy-furo-(3,4-c)-pyridine $R=(OCH_3)_3$
$n=4$
$X=Cl$
$A_1=A_2=$phenyl The method of example 15 was repeated but with 1,3-dihydro-3,3-diphenyl-4-chloro-6-(1-cyano-2-methyl-propyl)-7-hydroxy-furo-(3,4-c)-pyridine and N-(3,4,5-trimethoxyphenethyl)-N-methyl-4-aminobutyl chloride at 65° C. Yield was 44.6 g (62%) of a yellow powder melting at 169° C. (Tottoli), elemental analysis of which showed a very good correspondence with the formula $C_{40}H_{46}N_3O_5Cl$, HCl.

EXAMPLE 17

1,3-dihydro-3,3-di(p-chlorophenyl)-6-[1-cyano-isopropyl-N,(m,p-dimetoxy-phenethyl)-N-methyl-5-aminopentyl]-7-hydroxy-furo-(3,4-c)-pyridine $R=(OCH_3)_2$
$n=4$
$X=H$
$A_1=A_2=$ p-chlorophenyl The method of example 15 was repeated but with 1,3-dihydro-3,3-di(p-chlorophenyl)-6-(1-cyano-2-methyl-propyl)-7-hydroxy-furo-(3,4-c)-pyridine and the same 4-aminobutyl chloride, at 25° C. Yield was 39.2 g (54%) of a white product melting at 200°–202° C. (Tottoli), elemental analysis of which showed a good correspondence with the formula $C_{39}H_{43}N_3O_4Cl_2$.

EXAMPLE 18

1,3-dihydro-3-methyl-6-[1-cyano-1-methyl-N-(m,m,p-trimethoxy-phenethyl)-N-methyl-6-aminohexyl]-7-hydroxy-furo-(3,4-c)-pyridine $R=(OCH_3)_3$
$n=5$
$X=H$
$A_1=$ methyl
$A_2=H$ The method of example 4 was repeated but with 1,3-dihydro-3-methyl-6-(1-cyano-2-methyl-propyl)-7-hydroxy-furo-(3,4-c)-pyridine and N-(3,4,5-trimethoxy-phenethyl)-N-methyl-5-aminopentyl chloride at 40° C. Yield was 35.7 g (68%) of a pale yellow product melting at 213°–215° C. (Tottoli), elemental analysis of which showed a good correspondence with the formula $C_{30}H_{43}N_3O_5$.

EXAMPLE 19

1,3-dihydro-3-α-furyl-6-[1-cyano-1-isopropyl-N-(m,p-dimethoxy-phenethyl)-N-methyl-6-aminohexyl]-7-hydroxy-furo-(3,4-c)-pyridine $R=(OCH_3)_2$
$n=5$
$X=H$
$A_1=$ α-furyl
$A_2=H$ The method of example 5 was repeated but with 1,3-dihydro-3-α-furyl-6-(1-cyano-2-methyl-propyl)-7-hydroxy-furo-(3,4-c)-pyridine and N-(3,4-dimethoxy-phenethyl)-N-methyl-5-aminopentyl chloride at 30° C. Yield was 26 g (41%) of a white product melting at 154°–155° C. (Tottoli), elemental analysis of which showed a good correspondence with the formula $C_{32}H_{41}N_3O_5, C_2H_2O_4$.

EXAMPLE 20

1,3-dihydro-3,3-dimethyl-6-[1-cyano-1-isopropyl-N-(m,p-dimethoxy-phenethyl)-N-methyl-6-aminohexyl]-7-hydroxy-furo-(3,4-c)-pyridine $R=(OCH_3)_2$
$n=5$
$X=H$
$A_1=A_2=CH_3$ The method of example 19 was repeated but with 1,3-dihydro-3,3-dimethyl-6-(1-cyano-2-methyl-propyl)-7-hydroxy-furo-(3,4-c)-pyridine and the same 5-aminopentyl chloride, at 50° C. Yield was 36 g (60%) of a white crystalline product melting at 189°–191° C., elemental analysis of which showed a very good correspondence with the formula $C_{30}H_{43}N_3O_4, C_2H_2O_4$.

TOXICITY

Acute toxicity was researched, per os on rats and mice. Preliminary tests showed that no $LD_{50}$ was inferior to 650 mg/kg.

PHARMACOLOGY

The interest of the compounds of the invention has been evidenced by various tests.

(A) Isolated rabbit aorta strips treated by various contracturing agents.

This experiment was conducted according to the lines of the methods described by FURCHGOTT R. F. and BHADRAKOM S.—Reactions of strips of rabbit aorta to epinephrine, isopropylarterenol, sodium nitrite and other drugs. J. Pharmac. Exp. Therapeut., 1953, 108, 129–143, VAN ROSSUM J. M., Arch. Int. Pharmacodyn. Ther., 1963, 143, 299–330 and ARUNLAKSHANA, O. and SCHILD, H. O., 1959, Brit. J. Pharmac. 14, 48–58, using noradrenaline (NE), serotonine (5-HT), histamine (HIST), KCl and angiotensine II as agonists.

The compounds of the invention were compared to verapamil on these agonists and showed a similar range of action, with significative and generally comparable values of $PA_2$ (for NE, 5-HT and HIST) or of $IC_{50}$ (for KCl or angiotensine); however, they appear 5 to 10 times more active on 5-HT (average value for the compounds of the invention: $1.35 \times 10^{-8}$ and $7. \times 10^{-8}$ for verapamil). These compounds are competitive antagonists of the 5-HT receptor.

(B) Experimental ulcer induced by dimaprit.

23 Batches of each 5 male Sprague Dawley rats (150–200 g) were treated as follows:

Batches 1–20: The rats of each of these batches received 25 mg/kg per os of one of the compounds of the invention, suspended in 1 ml of physiologic serum.

Batches 21 and 22: The rats of these batches received 1 ml of physiologic serum.

Batch 23: The rats of this batch received 25 mg/kg of ranitidine, as reference compound, suspended in 1 ml of physiologic serum.

30 Minutes after this administration, all batches except batch 23, received, IP, 175 mg/kg dimaprit $(NH_2-(CNH)-(CH_2)_3-N(CH_3)_2)$.

Four hours after this treatment, the animals were killed and the ulcers counted. Batch 21 was a blank control and batch 22 the ulceration control. Results were given in percentage of protection compared with ulceration control. Protection by ranitidine was 39%, whereas protection for the compounds of the invention was comprised between 37 and 52,4%.

(C) Diuresis on rats

The diuretic activity has been researched on rats in comparison with a well known diuretic, furosemide, verapamil and a control; diuresis, elimination of $Na^+$, $K^+$ and of uric acid were determined on the compounds of the examples.

This experiment was conducted on batches of each 8 Wistar male rats (180–200 g) deprived from food and drink 16 hours before the experiment and during the same.

At zero time, each animal received, orally, in 2,5 ml/100 g of physiologic serum, 50 mg/kg of the compound to be tested. Rats are placed in individual metabolic cages and urines are collected for 6 hours. Na+, K+ and uric acid are dosed by usual methods. One batch was used as control (physiologic serum only), one for furosemide at 20 mg/kg, one for verapamil and one for each of the tested compounds, all at 50 mg/kg. The results are reported in the following table from which it clearly appears that the compounds of the invention are mild diuretics with a K+ retention and a good Na+ elimination. For uric acid, elimination is better than this of furosemide.

In the table, V is the volume of urine collected in 6 hours (in ml), Na+ and K+ are given in mEq/6 hours and uric acid in mMoles/6 hours. The figures are the average values of the animals of each batch. The percentages appearing in the column are by reference to control. The tested compounds are identified by the number of the corresponding example.

PRESENTATION—POSOLOGY

For oral use, the compounds of the invention may be presented in 50 mg dosage units associated with an appropriate diluent or carrier, in tablet, gelatine capsules or in suspension—Posology is of 1 or 2 units per diem.

For IV route, phials contain 10 mg of active compound and posology is 1 or 2 phials per diem.

TABLE

| COMPOUND | V | K+ | Na+ | Uric acid |
|---|---|---|---|---|
| CONTROL | 0.52 | 74.4 | 116.5 | 1.56 |
| FUROSEMIDE | 2.86 (+450%) | 138.1 (+85.6%) | 455.6 (+291%) | 2.01 (+28.8%) |
| VERAPAMIL | 0.68 (+31%) | 86.5 (+16.3%) | 193.3 (+65.9%) | 2.13 (+36.5%) |
| 1 | 1.32 (+154%) | 76.5 (−8.4%) | 309.8 (+94%) | 2.05 (+32.3%) |
| 5 | 0.85 (+63.5%) | 69.7 (−6.3%) | 225.8 (+93.8%) | 2.08 (+33.5%) |
| 6 | 0.60 (+15.4%) | 34.4 (−53.8%) | 200.1 (+72.5%) | 1.71 (+9%) |
| 9 | 0.56 (+7.7%) | 74.5 (0%) | 150.1 (+28.8%) | 1.77 (+13.5%) |
| 12 | 0.71 (+36.5%) | 68.3 (−8.2%) | 160 (+37.3%) | 1.89 (+21%) |
| 15 | 0.82 (+58.4%) | 76.6 (+3%) | 236.5 (+103%) | 1.83 (+17.5%) |

TABLE-continued

| COMPOUND | V | K+ | Na+ | Uric acid |
|---|---|---|---|---|
| 18 | 1.49 (+187.2%) | 72 (−3.2%) | 311.7 (+167.6%) | 2.20 (+41.1%) |
| 19 | 0.95 (+82.5%) | 49.5 (−33.4%) | 195.5 (+67.8%) | 1.85 (+18.4%) |

What is claimed is:

1. A 1,3-dihydro-6-[1-cyano-1-isopropyl-N-phenethyl-N-methyl-ω-aminoalkyl]-7-hydroxy-furo-(3,4-c)-pyridine derivative of the formula

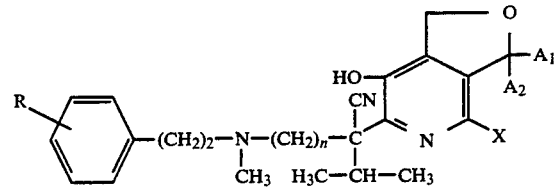

wherein, each of $A_1$ and $A_2$ independently represents a hydrogen atom, a straight chain saturated or unsaturated hydrocarbon group having from 1 to 5 carbon atoms, a thienyl or furyl group, a phenyl or phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α or β-alkoxy-N-pyrrolidinyl groups in which the alkoxy group has from 1 to 5 carbon atoms; R represents from one to three methoxy groups; n is 2,3,4 or 5; and X represents a hydrogen or chlorine atom; and pharmaceutically acceptable salts of such compounds.

2. A therapeutic composition of matter comprising as an essential ingredient therein a compound according to claim 1 in an amount effective to act as a calcium antagonist together with an appropriate diluent or carrier.

3. A therapeutic composition of matter comprising as an essential ingredient therein a compound according to claim 1 in an amount effective to act as a serotonin antagonist together with an appropriate diluent or carrier.

* * * * *